(12) United States Patent
Chang et al.

(10) Patent No.: US 7,367,196 B2
(45) Date of Patent: May 6, 2008

(54) SPINNING COLD PLASMA APPARATUS AND METHODS RELATING THERETO

(75) Inventors: Choongseock Chang, Princeton Junction, NJ (US); Jemo Kang, Princeton, NJ (US); Jaeyoung Park, Los Alamos, NM (US)

(73) Assignee: Princeton BioMeditech Corporation, Princeton, NJ (US)

( * ) Notice: Subject to any disclaimer, the term of this patent is extended or adjusted under 35 U.S.C. 154(b) by 284 days.

(21) Appl. No.: 11/064,300

(22) Filed: Feb. 23, 2005

(65) Prior Publication Data

US 2005/0274122 A1 Dec. 15, 2005

Related U.S. Application Data

(60) Provisional application No. 60/546,804, filed on Feb. 23, 2004.

(51) Int. Cl.
*F25B 9/02* (2006.01)
*H01J 13/28* (2006.01)
*H05B 31/26* (2006.01)
*H01L 21/322* (2006.01)

(52) U.S. Cl. .................. 62/5; 315/111.21; 438/474
(58) Field of Classification Search ............. 62/5; 438/474; 315/111.21
See application file for complete search history.

(56) References Cited

U.S. PATENT DOCUMENTS 5,265,801 A * 11/1993 Larson .................. 239/11
5,819,541 A * 10/1998 Tunkel et al. .................. 62/5
6,030,653 A * 2/2000 Rosenthal .................. 426/248
2003/0024806 A1* 2/2003 Foret .................. 204/164
2004/0099614 A1* 5/2004 Lehmann et al. .......... 210/787
2004/0168716 A1* 9/2004 Gritskevich et al. ........ 136/205
2004/0251211 A1* 12/2004 Suddath .................. 210/748
2006/0131282 A1* 6/2006 Miller et al. ............. 219/121.5

OTHER PUBLICATIONS

Print out from web site: http://en.wikipedia.org/wiki/Vortex_tube.

* cited by examiner

*Primary Examiner*—William C Doerrler
(74) *Attorney, Agent, or Firm*—Gerard P. Norton; Shahnam Sharareh; Fox Rothschild LLP

(57) ABSTRACT

Disclosed herein is an apparatus for generating a spinning cold plasma. A preferred embodiment of the spinning cold plasma apparatus is portable and includes a vortex tube having an inner wall to form a vortex reaction chamber. The vortex tube preferably has a cold gas outlet formed at a first end of the vortex tube and a hot gas outlet formed at a second end of the vortex tube. The vortex tube preferably has a plurality of gas inlet openings formed therein for directing pressurized gas tangentially to the inner wall into the vortex reaction chamber. A preferred embodiment of the portable spinning cold plasma apparatus also includes a valve positioned at least partially within the cold gas outlet and a valve positioned at least partially within the hot gas outlet. The portable device preferably also includes an ionizing device, such as an RF source or microwave source, for transmitting electromagnetic energy into the vortex reaction chamber to ionize pressurized gas therein. Additional apparatus and methods are also disclosed herein.

16 Claims, 1 Drawing Sheet

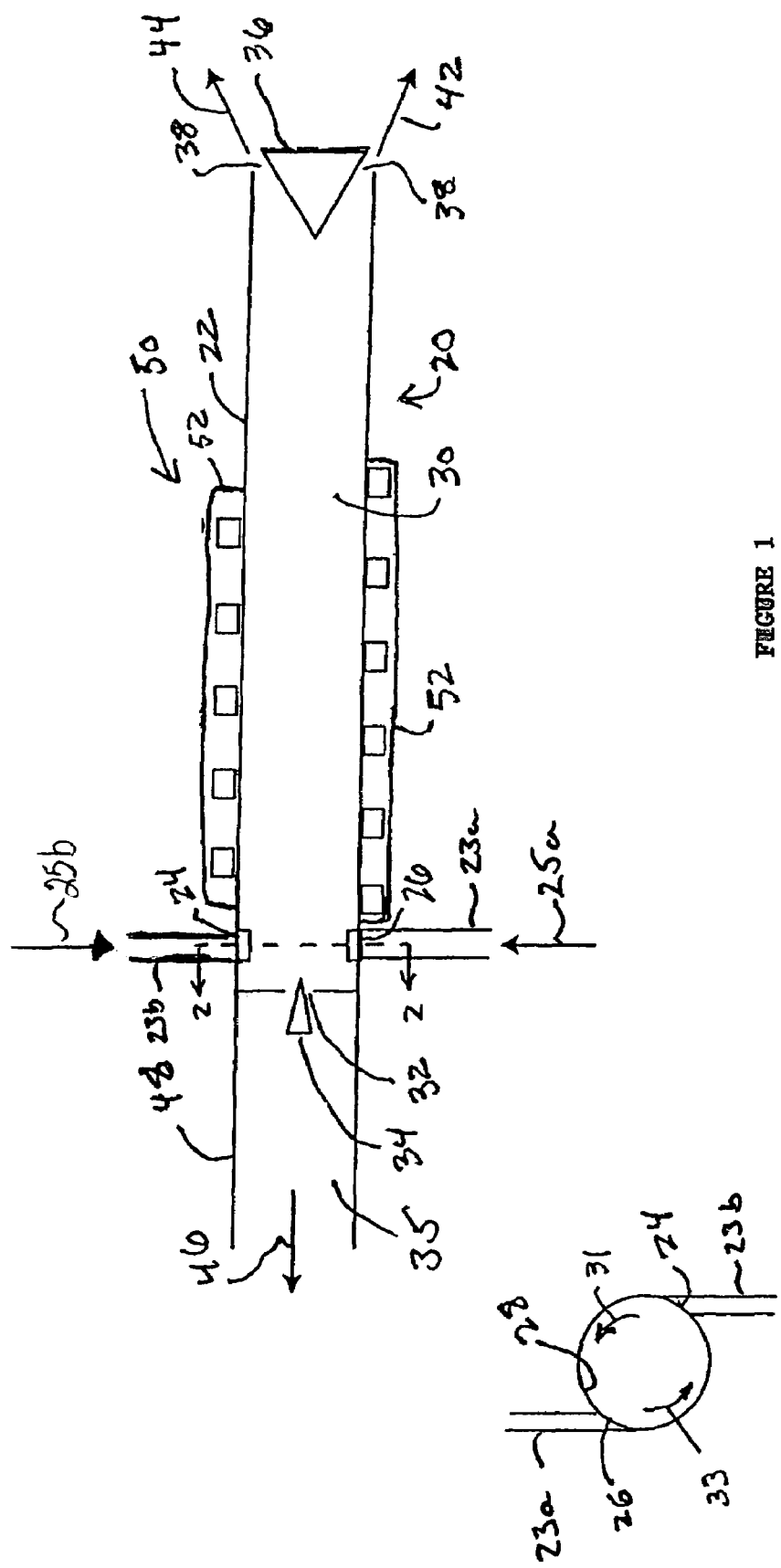

SPINNING COLD PLASMA APPARATUS AND METHODS RELATING THERETO

CROSS-REFERENCE TO RELATED APPLICATIONS

The current application claims the benefit under 35 U.S.C. § 119(e) of U.S. provisional patent application 60/546,804, filed on Feb. 23, 2004, which is hereby incorporated by reference in its entirety for all purposes.

FIELD OF THE INVENTION

The present invention relates to an apparatus and method for generating a spinning cold plasma. In another aspect, the invention provides methods for using the spinning cold plasma (SCP) including localized disinfecting of microbiological germs, treatment of surfaces (particularly delicate materials) in preparation for printing, treatment of coatings and enamel materials for dental applications, sterilization of packaging materials and medical/surgical equipment, surface modification of composites, and the like.

SUMMARY OF THE INVENTION

An apparatus for generating a spinning cold plasma is disclosed. A preferred embodiment of the apparatus is portable and includes a generally cylindrical vortex tube, a collar, a plurality of valves, and an ionizing device.

The vortex tube preferably has a vortex reaction chamber formed within an inner wall. The vortex tube preferably has a cold gas outlet positioned at a first end of the vortex tube and a hot gas outlet formed at a second end of the vortex tube. The vortex tube has at least one gas inlet opening, and preferably a plurality of gas inlet openings, formed therein for directing pressurized gas tangentially to the circumference of the inner wall into the vortex reaction chamber. Preferably, each of the gas inlet openings is substantially evenly spaced from one another along a curvature of the inner wall.

A preferred embodiment of the portable spinning cold plasma apparatus includes a plurality of valves, such as (1) a valve positioned at least partially within the cold gas outlet to regulate the flow of cold plasma from the vortex reaction chamber, and (2) a valve positioned at least partially within the hot gas outlet to regulate the flow of hot plasma from the vortex reaction chamber. A preferred embodiment of the portable spinning cold plasma apparatus also includes a collar extending from the vortex tube from the cold gas outlet.

A preferred embodiment of the portable spinning cold plasma apparatus includes an ionizing device for transmitting electromagnetic energy into the vortex reaction chamber to ionize pressurized gas therein. In some embodiments of the invention, the ionizing device comprises a microwave source and, in some embodiments of the invention, the ionizing device comprises an RF source. The ionizing device preferably includes a tunable inductive coupler for focusing the electromagnetic energy on a longitudinal central column region of the vortex reaction chamber.

Additional apparatus and methods are disclosed herein, including methods of using the preferred spinning cold plasma generating apparatus.

BRIEF DESCRIPTION OF THE DRAWINGS

The accompanying drawings, which are incorporated in and form a part of the specification, illustrate the embodiments of the present invention and, together with the description serve to explain the principles of the invention. In the drawings:

FIG. 1 is a schematic representation of a preferred embodiment of a portable spinning cold plasma apparatus; and FIG. 2 is a cross-sectional view taken along line 2-2 shown in FIG. 1.

DETAILED DESCRIPTION OF THE PREFERRED EMBODIMENTS

In describing a preferred embodiment of the invention illustrated in the drawings, specific terminology will be used for the sake of clarity. However, the invention is not intended to be limited to the specific terms so selected, and it is to be understood that each specific term includes all technical equivalents which operate in a similar manner to accomplish a similar purpose.

With reference to FIGS. 1 and 2, a spinning cold plasma source apparatus is disclosed. In a preferred embodiment, the spinning cold plasma apparatus is a portable device for generating a spinning cold plasma that comprises a vortex generator 20 and an ionizing device, such as radio frequency (RF) source 50, a microwave source (not shown), and/or another ionizing device.

Vortex generator 20 comprises an elongated vortex tube 22 and a source of pressurized gas (not show). Vortex tubes of known design such as "reverse-flow" or "uniflow" design may be used. FIG. 1 illustrates use of the preferred reverse-flow vortex tube. Vortex tube 22 comprises a longitudinal vortex reaction chamber 30, gas inlet openings 24 and 26, cold gas outlet 32 at one end of vortex tube 22 for the discharge of cold gas flow, and hot gas outlets 38 at the opposite end of vortex tube 22 for the discharge of hot gas flow. Preferably, cold gas outlet 32 and hot gas outlets 38 are regulated by valves 34 and 36, respectively. Pressurized gas is directed tangentially into vortex tube 20 through gas inlet openings 24 and 26 along arrows 25a and 25b from gas inlet passages 23a and 23b. Gas inlet openings 24 and 26 are aligned tangentially to the inner wall 28 of vortex tube 22 thereby causing a flow of gas in the direction of arrows 31 and 33 within vortex reaction chamber 30. Although gas inlet passages 23a and 23b and the source of pressurized gas (not shown) are preferably part of vortex generator 20, in some embodiments they may be part of one or more external structures.

In the preferred portable device illustrated in FIG. 1, vortex tube 22 has a longitudinal length of about two hundred (200) millimeters and a diameter of about twenty (20) millimeters. Preferably, portable device 10 has a collar 35 of similar diameter and about twenty-five (25) millimeters in length at the cold gas flow end of vortex tube 22. However, each of the components of the portable spinning cold plasma device may have any suitable dimensions.

As a result of injection of pressurized gas through gas inlet openings 24 and 26, a forced vortex flow within vortex reaction chamber 30 is generated. The gas is preferably pressurized to three (3) to ten (10) atmospheres thereby causing a supersonic rotational flow of high pressure within vortex reaction chamber 30. As a result, the gas density in the longitudinal center column of vortex tube 22 is much lower than along the periphery of inner wall 28 of vortex tube 22. The rotational speed of the gas in vortex reaction chamber 30 is preferably in the sonic range.

RF source 50 is designed to ionize the less dense, longitudinal central column of gas within vortex reaction chamber 30 through inductive coupling. Any suitable configuration as is known in the art may be used. RF source 50 comprises, for example, an RF power supply (not shown), a tuning network (not shown), and an RF coil winding 52. FIG. 1 illustrates the use of RF coil winding 52 on the exterior of vortex tube 22 in the region of vortex reaction chamber 30. Frequencies in the range of about 10 kHz to 27 MHz, preferably in the range of 50 kHz to 1 MHz, and most preferably in the range of about 100 to 500 kHz, may be used. The power requirement will vary depending on the application. In the portable device illustrated in FIG. 1, it is contemplated that power will be in the range of about 400 W to 600 W, most preferable about 500 W.

In another preferred embodiment of the invention, portable spinning cold plasma device includes a microwave source (not shown) designed to ionize the less dense, longitudinal central column of gas within vortex reaction chamber 30. The microwave source preferably comprises a microwave generator. Preferred microwave frequencies are in a range including two-thousand four-hundred and fifty (2,450) megahertz.

Any suitable gas or mixture of gases known to generate a stable plasma be used, such as Argon, natural air, $CO_2$, $NF_3$, $CF_4$, $SF_6$, Nitrogen-based gases, and mixtures thereof A preferred gas is a mixture of Argon and Oxygen.

In operation, the apparatus of the present invention generates a "cold" plasma and cold neutral radicals, i.e., a plasma which has a temperature of less than about 100° C. The RF source ionizes the gas in the lower temperature, less dense, central column in vortex reaction chamber 30. The exact temperature of the plasma is a function of several parameters such as power and gas flow. Preferably, ionized plasma having a temperature of about 70° C. or lower is achieved. The thusly ionized cold plasma and neutral radicals are discharged through cold gas outlet 32 in the direction of arrow 46. Hot plasma is discharged at the opposite end through hot gas outlet 38 in the direction of arrows 42 and 44. It is highly desirable to concentrate the discharge power coupling to the central cold column of gas and to minimize the power coupling to hot peripheral gas. By configuring the RF coupling in this manner, the overall power efficiency to the cold radical generation is improved.

It is believed that the high gas rotation speed (when compared, for example, to plasma torch or arc spray) generates a less dense gas column in the center, absorbs the RF power preferentially, and induces the cold plasma and radical flow through cold gas outlet 32. Since the radicals are flowing out at a high speed from cold gas outlet 32, it is believed that their survival distance is enhanced in proportion to the flow speed.

The high-speed spinning cold plasma (SCP) generated by the device of the present invention may be beneficially used in a number of applications. One important application is the use of SCP to sanitize surfaces by killing microbiological germs such as, for example, anthrax spores. SCP has a relatively low temperature (50°-100° C.) when compared to other sterilization agents such as steam. SCP can also be generated such that it is substantially free of water vapor. Therefore, SCP can be used to sterilize devices such as computers, keyboards, or other electronic equipment which cannot be sanitized with other sterilization agents that would otherwise damage the equipment or could be hazardous to handle. SCP may also be used to sterilize laboratory, medical and surgical equipment without the use of autoclaves or other expensive equipment.

SCP may also used to sterilize enclosed spaces such operating rooms or laboratories. If properly scaled, SCP may be used to sterilize entire facilities by forcing it through the ventilation system.

Another important application is the surface treatment of substrates for bonding or printing. Because of its relatively low temperature, SCP may be used to improve the dyeability or wettability of plastic and fiber substrates. SCP is particularly well suited for surface treatment of delicate substrates such silk for printing which heretofore could not be treated with plasma because of potential damage to the substrate. SCP may also be used to modify surfaces to enhance bonding, e.g., in dental applications or formation of composites, by making the surfaces more active chemically.

The spinning cold plasma apparatus of the present invention also eliminates the requirement present in many prior art plasma treatment systems to carry out the plasma treatment in an enclosed or vacuum environment.

What is claimed is:

1. A spinning cold plasma apparatus, comprising:
   a vortex tube having a vortex reaction chamber, an inner wall, and a generated plasma, wherein the vortex tube having a cold gas outlet formed at a first end of the vortex tube and a hot gas outlet formed at a second end of the vortex tube, and the vortex tube having at least one gas inlet opening formed in the vortex tube for directing pressurized gas tangentially to the inner wall into the vortex reaction chamber;
   a valve positioned at least partially within the cold gas outlet to regulate the flow of cold plasma from the vortex reaction chamber; and
   an ionizing device for transmitting electromagnetic energy into the vortex reaction chamber to ionize pressurized gas therein, wherein the ionizing device is a source selected from the group consisting of a RF source, and a microwave source capable of forming plasma in the central region of the reaction chamber of said vortex tube.

2. The spinning cold plasma apparatus of claim 1, wherein the RF source comprises a tunable inductive coupler adapted to focus electromagnetic energy on a longitudinal central column region of the vortex reaction chamber.

3. The spinning cold plasma apparatus of claim 1, wherein the vortex tube comprises a plurality of gas inlet openings.

4. The spinning cold plasma apparatus of claim 3, comprising at least one source of pressurized gas in fluid communication with the plurality of gas inlet passages.

5. The spinning cold plasma apparatus of claim 1, comprising a collar extending from the cold gas outlet.

6. The spinning cold plasma apparatus of claim 1, wherein the vortex tube comprises a reverse-flow vortex tube.

7. A method of producing a spinning cold plasma, comprising:
   directing a pressurized gas into a vortex chamber of a vortex tube to induce a rotational flow of higher-density pressurized gas along an inner wall of the chamber and a lower-density pressurized gas at the longitudinal center column of the reaction chamber of the vortex tube;
   ionizing the lower-density pressurized gas;
   generating spinning cold plasma in the central region of the reaction chamber of said vortex tube.

8. The method of claim 7, further comprising the step of: transmitting electromagnetic energy into the chamber.

9. The method of claim 8, further comprising the step of: focusing the electromagnetic energy on the longitudinal center column of lower-density pressurized gas.

10. The method of claim 8, wherein the electromagnetic energy is transmitted from an RF source.

11. The method of claim 8, wherein the electromagnetic energy is transmitted from a microwave source.

12. The method of claim 7, wherein the pressurized gas is selected from the group consisting of Argon, natural air, $CO_2$, $NF_3$, $CF_4$, $SF_6$, a Nitrogen-based gas, and mixtures thereof.

13. A method of disinfecting a surface, comprising applying the spinning cold plasma produced by the method of claim 7 to the surface of interest.

14. A method of increasing the wettability of a substrate, comprising
   (a) directing a pressurized gas into a vortex chamber to induce a rotational flow of higher-density pressurized gas along an inner wall of the chamber and a lower-density pressurized gas at the longitudinal center of the reaction chamber of:
   (b) transmitting electromagnetic energy into the chamber;
   (c) focusing the electromagnetic energy on the longitudinal center reaction column of lower-density pressurized gas, wherein the electromagnetic energy is transmitted from an RF source or a microwave source or a combination thereof;
   (d) ionizing the lower-density pressurized gas to produce the spinning cold plasma at the center region of the reaction chamber of the vortex tube; and
   (e) applying the spinning cold plasma to the substrate.

15. The apparatus of claim 1, wherein only a single ionizing device is employed to generate the plasma.

16. The method of claim 7, wherein only a single ionizing device is employed to generate the plasma.

* * * * *